United States Patent [19]

Horn

[11] Patent Number: 4,910,718
[45] Date of Patent: Mar. 20, 1990

[54] METHOD AND APPARATUS FOR ACOUSTIC EMISSION MONITORING

[75] Inventor: Michael Horn, South Setauket, N.Y.

[73] Assignee: Grumman Aerospace Corporation, Bethpage, N.Y.

[21] Appl. No.: 253,644

[22] Filed: Oct. 5, 1988

[51] Int. Cl.[4] ............................................. G01S 3/80
[52] U.S. Cl. ..................................... 367/124; 367/127; 367/129; 367/907
[58] Field of Search ............... 367/124, 127, 129, 118, 367/907; 73/572, 583

[56] References Cited

U.S. PATENT DOCUMENTS

| | | |
|---|---|---|
| 1,842,342 | 1/1932 | Eaton . |
| 2,628,335 | 2/1953 | Drake . |
| 2,932,189 | 4/1960 | Carlin . |
| 3,019,637 | 2/1962 | Cook et al. . |
| 3,383,651 | 5/1968 | Koblick . |
| 3,441,904 | 4/1969 | Wilson . |
| 3,492,634 | 1/1970 | Massa . |
| 3,559,161 | 1/1971 | Raudsep . |
| 3,683,680 | 8/1972 | Johnson et al. . |
| 3,723,960 | 3/1973 | Harris . |
| 3,792,424 | 2/1974 | Nakatsuji et al. . |
| 3,837,202 | 9/1974 | Hetherington et al. . |
| 3,886,553 | 5/1975 | Bates ................................. 367/127 |
| 3,924,450 | 12/1975 | Uchiyama et al. . |
| 3,990,300 | 11/1976 | Kossoff . |
| 4,137,779 | 2/1979 | Wüstenberg et al. . |
| 4,198,704 | 4/1980 | Munson ............................. 367/125 |
| 4,362,059 | 12/1982 | Zwyssig . |
| 4,399,702 | 8/1983 | Suzuki . |
| 4,404,853 | 9/1983 | Livingston . |
| 4,509,369 | 4/1985 | Kuljis et al. . |
| 4,522,064 | 6/1985 | McMillan . |
| 4,601,025 | 7/1986 | Lea .................................... 367/127 |

Primary Examiner—Thomas H. Tarcza
Assistant Examiner—Daniel T. Pihulic
Attorney, Agent, or Firm—Pollock, VandeSande & Priddy

[57] ABSTRACT

In order to locate a source of acoustic emissions, two multi-element transducers are employed. The elements of each transducer are subjected to an impinging acoustic wave at different moment in time depending upon the angle of the wave. Outputs from the elements of each transducer are compared with a look-up table to determine the angle. Then, another look-up table is used to determine the X-Y intersection of impinging wave angles from both transducers which locates the source.

3 Claims, 2 Drawing Sheets

METHOD AND APPARATUS FOR ACOUSTIC EMISSION MONITORING

FIELD OF THE INVENTION

The present invention relates to acoustic emission monitoring systems, and more particularly to such a system for locating a source in a structural member which creates acoustic waves.

BRIEF DESCRIPTION OF THE PRIOR ART

In the art of acoustic emission monitoring, a problem arises in determining the direction from which an acoustic signal emanates. Several transducers placed around an area to be monitored, such as an aircraft structure, can be "hit" by signals from a plurality of sources, both inside and outside the area of interest. In order to determine the source location of acoustic signals, the data acquisition portion of a signal processing system waits for one transducer to be "hit" and calculates the difference in time until another transducer is "hit" thus generating a $\Delta T$. The $\Delta T$ is used to determine where, along two intersecting hyperbolas, the source is located. Unfortunately, the calculation produces locations of widely varying regions of a test area. This is due to the pick-up of noise which causes false detection.

BRIEF DESCRIPTION OF THE PRESENT INVENTION

The present invention succeeds in eliminating the effects of noise by assuring that the detected signal source is located on the structure and within an area of interest. The structure of the present invention utilizes a minimum of two transducers, both of which incorporate an array of three or more crystal elements. By deploying at least two of these transducer arrays, acoustic source location by vector analysis can be achieved. The individual array transducer, when "hit" by a signal, will respond according to which element of the array is hit first, second, etc. By calculating the relative $\Delta T$ for the individual array elements, the location point of the source can be deduced without the inaccuracies generated by the prior art method of computing intersecting hyperbolas. By comparing the incident directions of detected signals of at least two transducers located within the same monitored zone, an intersection of azimuth lines can be employed to obtain the point of intersection of an acoustic emission source.

The present invention has particular applicability in testing the structural integrity of aircraft. When minor flaws develop in the aircraft structure, elastic acoustic waves are generated and, of course, it is most important to be able to locate the origin of the acoustic emission source so that appropriate repairs may be made. The present invention offers this capability.

BRIEF DESCRIPTION OF THE FIGURES

The above-mentioned objects and advantages of the present invention will be more clearly understood when considered in conjunction with the accompanying drawings, in which.

DETAILED DESCRIPTION OF THE INVENTION

Figure 2:
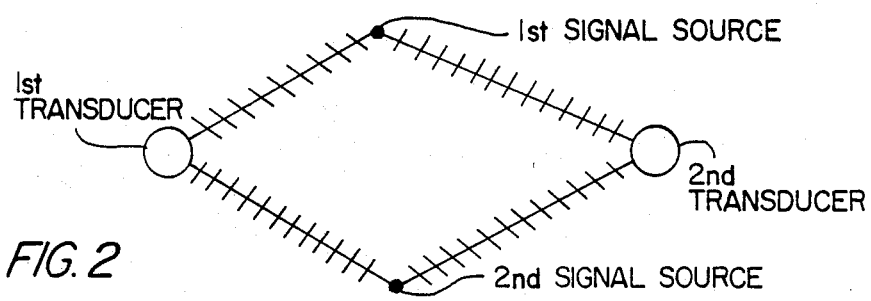
FIG. 2 is a graphical representation of transducer placement relative to signal sources.

In order to explain the concept of the present invention, reference is made to FIG. 2 which schematically illustrates transducer placement relative to signal sources. It is assumed that acoustic emissions are generated at the first and second signal sources at different instants of time. The purpose of graphically illustrating the existence of two signal sources is to emphasize the fact that the present invention is operable for more than one signal source as opposed to prevalent prior art approaches. Let us assume that the first signal source generates acoustic emissions, parallel acoustic waves will be propagated shortly after leaving the signal source as they travel toward both the first and second illustrated transducers. Each transducer is, in effect, a package of multiple transducer elements which detect impinging waves independently. As the elements of the first transducer receive the impinging wave from the first signal source, each element will receive a "hit" from the impinging wave at a different instant of time. The order of the transducer element "hits" depends upon the angle of the impinging wave. As will be explained hereinafter, a look-up table is created for experimentally correlating impinging wave angle as a function of time-delayed "hits" of the various elements in the first transducer. The creation of such a look-up table is well within the skill of a technician in the art and simply requires the straightforward adjustment of impinging angle and recording of consequent time delays and sequence of "hits" of the various transducer elements in the first transducer.

A similar look-up table is developed for the second transducer as a result of the acoustic emissions directed toward it from the first signal source. Since the location of the two transducers themselves is fixed and the impinging angles of the waves from the first signal source can be determined for both transducers, a simple geometric calculation will determine the point of intersection of both illustrated elastic waves which determines the exact location of the first signal source. Similar determinations may be made for the location of the second signal source when acoustic emissions from that source are detected by the elements of the first and second transducers.

Figure 1:
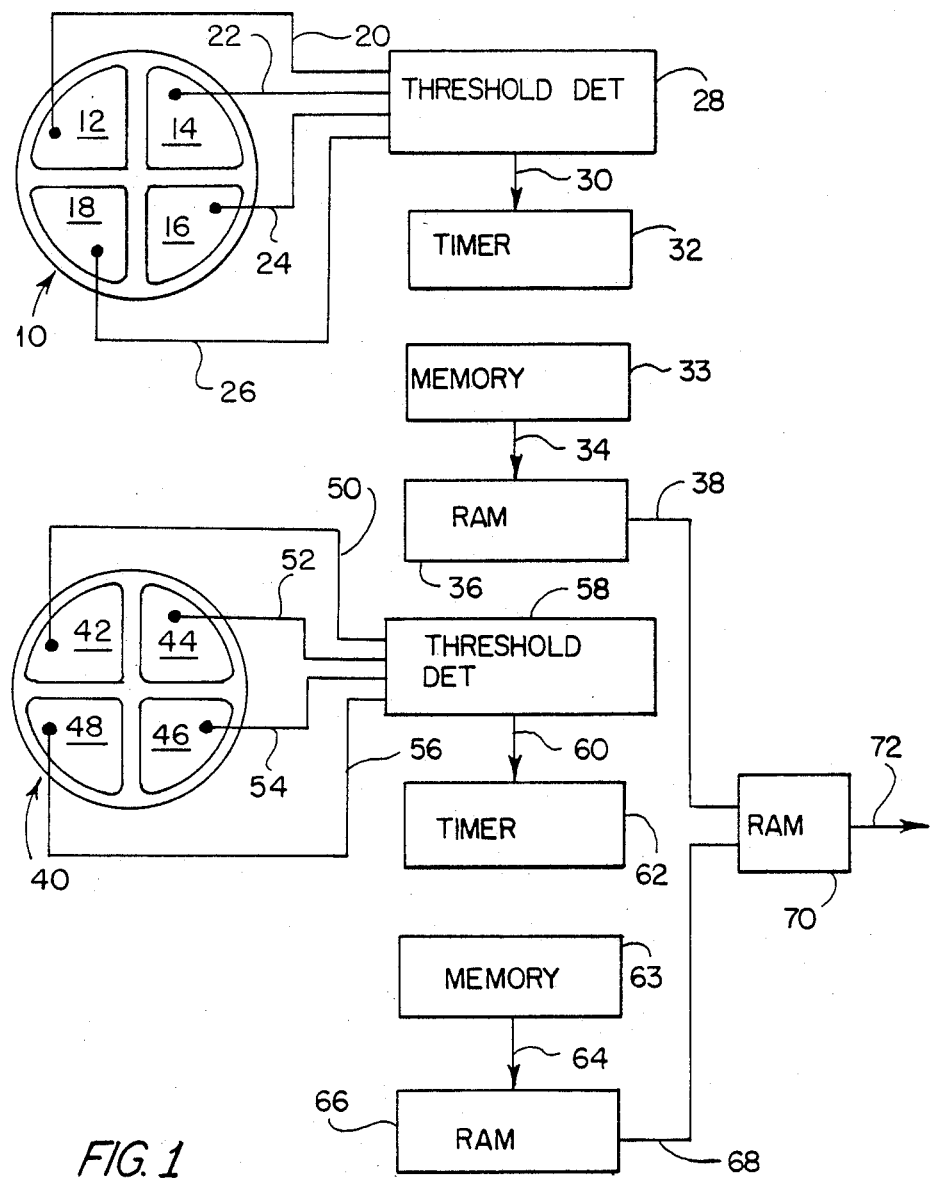
FIG. 1 is a block diagram illustrating a system of the present invention.
Figure 3:
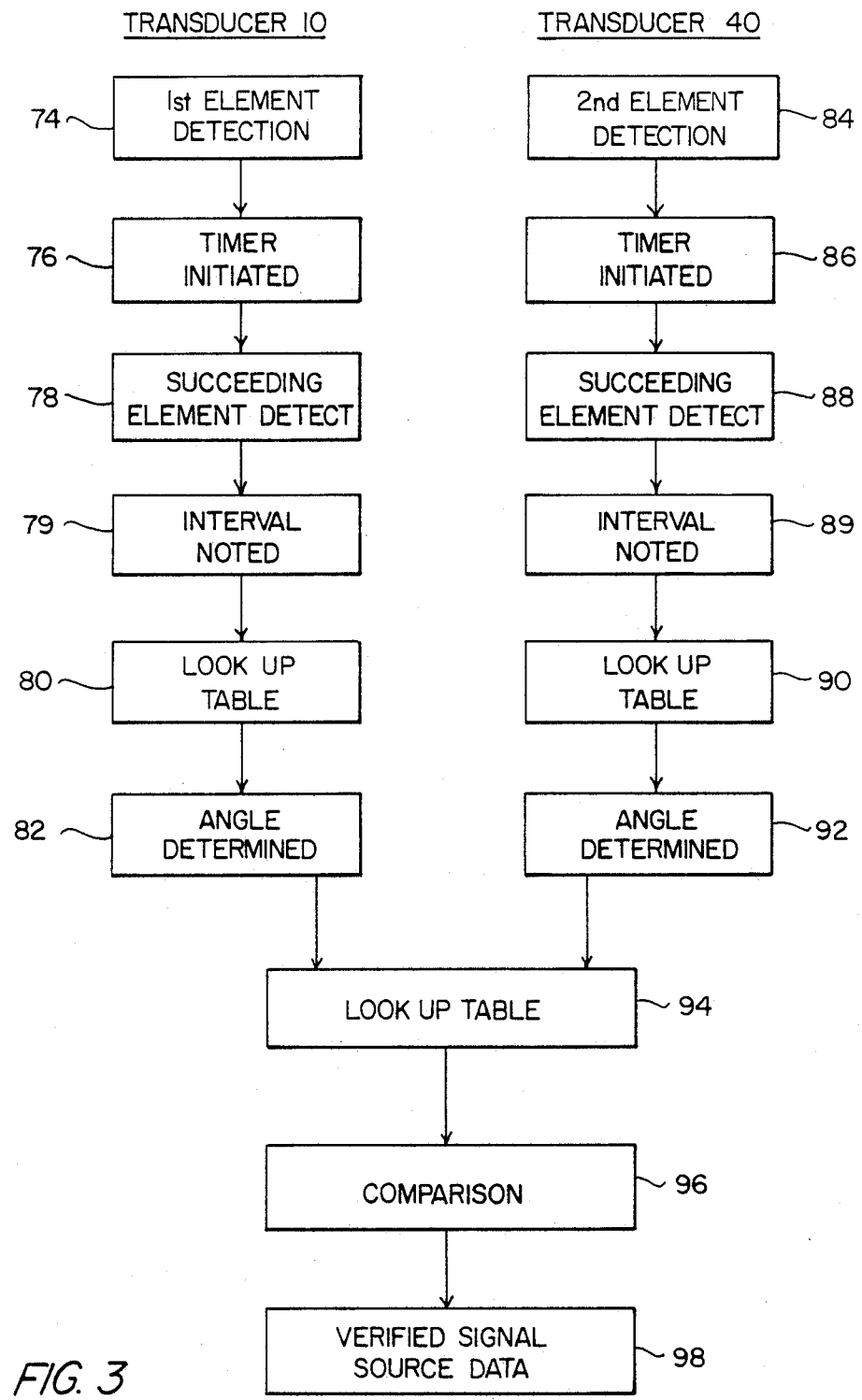
FIG. 3 is a schematic flow chart for operation of the present invention.

FIG. 1 illustrates in block diagram form the structure for the present invention. Reference numeral 10 generally denotes a first transducer which must necessarily include three or more segment elements but which is illustrated as having four elements 12, 14, 16 and 18. The transducer elements themselves are of conventional material capable of detecting acoustic emissions. However, an aspect of the patentability of the present invention is the inclusion of a plurality of transducer elements within a single package and having acoustically exposed surfaces in the same plane. The individual elements have respective output leads 20, 22, 24 and 26 that may be introduced into a threshold detector network 28 which detects the occurrence of an acoustic emission "hit" across a corresponding transducer element. As previously explained in connection with FIG. 2, an acoustic elastic wave directed across the transducer 10 will "hit" the various transducer elements at different instants of time, depending upon the angle across which the acoustic elastic wave is directed from a source of the acoustic emissions. Time intervals after the first "hit" of an impinging acoustic elastic wave at transducer 10 continually trigger timer 32 and the various time intervals and corresponding transducer elements affected are stored in memory 33. These steps are indicated in the flow chart of FIG. 3 and are identified as steps 74, 76, 78 and 79.

As previously explained in connection with FIG. 2, the impinging angle of the acoustic emission wave may be determined from the sequence of transducer elements affected and the various time intervals between transducer element "hits." A look-up table is provided in RAM 36, comparison data therefrom providing the determination of angle. These steps are indicated at 80 and 82 in FIG. 3. The determined angle relative to transducer 10 is then digitally provided at output 38 of RAM 36.

As was previously explained in connection with FIG. 2, a minimum of two transducers is necessary to locate the source of an acoustic emission. Thus, a second transducer 40 is provided which may be identical to transducer 10 and therefore may be equipped with elements 42, 44, 46 and 48. The reader is reminded that, although four transducer elements are located in FIG. 1, a minimum of three is theoretically required while a greater number will provide more accurate resolution of angle. The individual elements of transducer 40 have individual output leads 50, 52, 54 and 56 feeding a threshold detector 58.

The circuitry thus far described is identical to that associated with the first-explained transducer 10 and the following described circuitry in connection with the second transducer is likewise identical to that of the first transducer. Thus, the threshold detector 58 has its output connected to a timer 62 for timing intervals as the various transducer elements are affected. This corresponds with steps 84, 86, 88 and 89 of FIG. 3. A memory 63 is again provided to store the sequence of affected transducer elements and their corresponding time intervals. The memory 63 is connected to a RAM 66, via connection 64 for again permitting a look-up table to be employed for determining the impinging angle from the first signal source relative to transducer 40. At this stage, the reader is reminded that both transducers 10 and 40 are simultaneously monitoring acoustic emissions from a single source. At a different instant of time, a second or subsequent signal source may generate acoustic emissions; and again, both transducers 10 and 40 will monitor those emissions.

A final look-up table may be stored in RAM 70 for again correlating the individually determined wave angles from transducers 10 and 40 with a point of intersection based upon basic geometric principles. Thus, the output 72 from RAM 70 may provide digital data regarding the X-Y coordinates of an acoustic emissions source. This is indicated by look-up table 94 in FIG. 3.

In order to assure that the data of output 72 does not include erroneous results, it may be important to compare that output data with the known X-Y boundaries of a zone being monitored. Accordingly, as indicated by step 96 in FIG. 3, a comparison may be made between the final results and the boundary data. If a signal source has been measured outside such a zone, this data may be ignored as erroneous. Accordingly, as indicated by reference numeral 98 in FIG. 3, the comparison at step 96 may assure verified signal source data.

According to the description of the invention as just presented, it will be appreciated that comparing the directions associated with two transducers monitoring a single active source of acoustic emissions, an intersection of azimuth lines may be employed to obtain the X-Y location of the acoustic emission source. Further, the present invention allows for a comparison of the results with the X-Y coordinates of a known boundary being monitored so that derived data may be verified.

It should be understood that the invention is not limited to the exact details of construction shown and described herein for obvious modifications will occur to persons skilled in the art.

I claim:

1. A system for monitoring acoustic emissions from a source, the system comprising:
   a first single transducer array which includes at least three transducer elements mounted adjacent one another in a single package and having acoustically exposed surfaces in the same plane;
   first threshold detecting means for sensing when each respective element receives an impinging acoustic wave from the source;
   first means connected at its input to the threshold detecting means for measuring the time of arrival of the sensed acoustic wave at each element;
   first means connected at its input to the measuring means for storing data representing the sequence and time periods during which the individual elements are affected by the wave;
   first memory means for storing a first look-up table, the first memory means comparing the stored data with the contents of the first look-up table for determining a corresponding angular direction of the wave relative to the first transducer array;
   a second single transducer array which includes at least three transducer elements mounted adjacent one another in a single package and having acoustically exposed surfaces in the same plane;
   second threshold detecting means for sensing when each respective second transducer element receives an impinging acoustic wave from the source;
   second means connected at its input to the second threshold detecting means for measuring the time of arrival of the sensed acoustic wave at each element of the second transducer array;
   second means connected at its input to the second measuring means for storing data representing the sequence and time periods during which the individual elements are affected by the wave; and
   second memory means for storing a second look-up table, the second memory means comparing the stored data of the second storing means with the contents of the second look-up table for determining the angular direction of the wave relative to the second transducer array;
   third memory means for storing a third look-up table for comparing the first and second directions obtained from the first and second memory means with the contents of the third look-up table, the third memory means determining the X-Y intersection of the first and second waves incident to the transducer arrays thereby establishing the location of the source.

2. A method for monitoring acoustic emissions from a source, the method comprising the steps:
   positioning a first single multi-element transducer array within a zone to be monitored, multi-elements mounted adjacent one another in a single package and having acoustically exposed surfaces in the same plane;

sensing when each respective element receives an impinging acoustic wave from the source;

measuring the time of arrival of the sensed acoustic wave at each element;

storing data representing the sequence and time periods during which the individual elements are affected by the wave;

storing a first look-up table for comparing the stored data with the contents of the first look-up table for determining the angular direction of the wave relative to the first transducer array;

positioning a second single multi-element transducer array within a zone to be monitored, multi-elements mounted adjacent one another in a single package and having acoustically exposed surfaces in the same plane;

sensing when each respective element of the second transducer array receives an impinging acoustic wave from the source;

measuring the time of arrival of the sensed acoustic wave at each element of the second transducer array;

storing data representing the sequence and time periods during which the individual elements of the second transducer array are affected by the wave;

storing a second look-up table for comparing the stored data with the contents of the second look-up table for determining the angular direction of the wave relative to the second transducer array;

storing third look-up table for comparing the first and second angular directions obtained from the waves relative to the first and second transducer arrays with the contents of the third look-up table for determining the X-Y intersection of the first and second incident to the transducer arrays thereby establishing the location of the source.

3. The method set forth in claim 2 together with the step of comparing the derived X-Y intersection with a preselected boundary; and rejecting any derived X-Y intersection outside the boundary.

* * * * *

UNITED STATES PATENT AND TRADEMARK OFFICE
CERTIFICATE OF CORRECTION

PATENT NO. : 4,910,718
DATED : March 20, 1990
INVENTOR(S) : Michael Horn It is certified that error appears in the above-identified patent and that said Letters Patent is hereby corrected as shown below:

In the Abstract, line 4, change "moment" to --moments--.

Column 6, line 11, after "storing" insert --a--.

Column 6, line 16, after "second" insert --waves--.

Signed and Sealed this

Second Day of April, 1991

*Attest:*

HARRY F. MANBECK, JR.

*Attesting Officer*   *Commissioner of Patents and Trademarks*